United States Patent [19]
Slate et al.

[11] Patent Number: 5,605,152
[45] Date of Patent: Feb. 25, 1997

[54] OPTICAL GLUCOSE SENSOR

[75] Inventors: John B. Slate, San Diego; Peter C. Lord, Valencia, both of Calif.

[73] Assignee: MiniMed Inc., Sylmar, Calif.

[21] Appl. No.: 276,453

[22] Filed: Jul. 18, 1994

[51] Int. Cl.$^6$ ................................ A61B 5/00; G02B 6/00
[52] U.S. Cl. .......................... 128/634; 128/637; 356/39; 422/82.08; 436/172
[58] Field of Search .................................. 128/634, 632, 128/633, 637; 422/58, 55, 82.08; 436/805, 95, 136, 138, 172; 356/445, 39; 435/14

[56] References Cited

U.S. PATENT DOCUMENTS

| | | |
|---|---|---|
| 3,814,081 | 6/1974 | Mori . |
| 3,839,154 | 10/1974 | Messing . |
| 3,857,771 | 12/1974 | Sternberg . |
| 3,919,051 | 11/1975 | Koch et al. . |
| 3,992,631 | 11/1976 | Harte . |
| 4,056,724 | 11/1977 | Harte . |
| 4,231,754 | 11/1980 | Vogelhut . |
| 4,269,938 | 5/1981 | Frank . |
| 4,340,669 | 7/1982 | Bauer . |
| 4,353,984 | 10/1982 | Yamada et al. . |
| 4,476,870 | 10/1984 | Peterson et al. . |
| 4,517,291 | 5/1985 | Seago . |
| 4,548,907 | 10/1985 | Seitz et al. . |
| 4,557,900 | 12/1985 | Heitzmann . |
| 4,560,248 | 12/1985 | Cramp et al. ........................ 128/634 |
| 4,606,351 | 8/1986 | Lubbers . |
| 4,680,268 | 7/1987 | Clark, Jr. ........................... 128/635 |
| 4,721,677 | 1/1988 | Clark, Jr. ........................... 128/635 |
| 4,974,929 | 12/1990 | Curry ................................. 128/637 |
| 4,981,779 | 1/1991 | Wagner .............................. 128/637 |
| 5,001,054 | 3/1991 | Wagner .............................. 128/637 |
| 5,409,666 | 4/1995 | Nagel et al. ........................ 436/172 |
| 5,462,880 | 10/1995 | Kane et al. ......................... 436/172 |

OTHER PUBLICATIONS

1985 American Chemical Society—Two-Dimensional Enzyme Elect. Reprint from Analytical Chem.
Diabetes Care. vol. 5 No. 3 May–Jun. 1982.
David A. Gough, Ph.D.—The UCSD Implantable Glucose and Oxygen Sensor Tech. Feb. 3, 1986.
In Vitro Stability of an Oxygen Sensor—Analytical Chemistry, 1987.
Optical Glucose Sensor Based on Reversible Competitive Binding—Symposium on Biosensors—1984.
IEEE Transactions on Biomedical Engineering vol. 35 No. 7 Jul. 1988.

*Primary Examiner*—Angela D. Sykes
*Assistant Examiner*—Eric F. Winakur
*Attorney, Agent, or Firm*—Kelly Bauersfeld & Lowry

[57] ABSTRACT

An improved glucose sensor adapted for in vivo implantation includes one or more optical fiber optrodes mounted within a semipermeable probe housing designed for differential diffusion of glucose and oxygen. In a preferred form, an enzyme optrode comprises an optical fiber with an enzyme coating such as glucose oxidase for catalyzing glucose in the presence of oxygen ($O_2$) to produce gluconic acid and hydrogen peroxide. An oxygen sensitive coating such as a fluorescent dye is provided on the enzyme optrode in close proximity with the enzymatic reaction, and also on a reference optrode at a position spaced substantially from the enzymatic reaction. Optical monitoring of the fluorescent activity of the optrode coatings provides an indication of oxygen depletion as a result of the enzymatic reaction, and thus also indicates glucose concentration level. The semipermeable housing is designed to ensure that the reaction proceeds with a stoichiometric excess of oxygen ($O_2$).

12 Claims, 1 Drawing Sheet

OPTICAL GLUCOSE SENSOR

BACKGROUND OF THE INVENTION

This invention relates generally to glucose sensors for monitoring glucose concentration level in a patient fluid, such as blood. More specifically, this invention relates to an improved glucose sensor having one or more optical fiber optrodes for monitoring glucose concentration, wherein the optrodes are incorporated into a compact sensor probe adapted for in vivo implantation.

A variety of test systems and methods are known in the medical arts for measuring glucose concentration in a patient body fluid, such as blood, urine, etc. Glucose monitoring provides a valuable indicator of patient condition, and is particularly important for diabetic patients to provide an indicator of patient response to and/or compliance with a prescribed treatment regimen.

In accordance with one known and commonly used glucose detection method, an enzymatic assay is performed wherein an enzyme such as glucose oxidase is used to catalyze glucose within a patient fluid in the presence of oxygen ($O_2$). This enzymatic reaction produces gluconic acid and hydrogen peroxide ($H_2O_2$). Monitoring of the patient fluid before and after the enzymatic reaction can provide an indication of oxygen ($O_2$) depletion which can be correlated substantially linearly with glucose concentration level. In the past, oxygen depletion has been measured by monitoring fluid conductivity changes. Oxygen concentration levels in body fluids have also been measured by optical monitoring of a fluorescing dye having a light output responsive to oxygen level. The enzymatic assay, as described above, has typically been performed on a patient fluid which has been drawn from the patient and transported to a medical laboratory.

In recent years, significant interest has arisen in the development of a glucose sensor adapted for in vivo implantation to provide continuous or frequent glucose measurements, particularly for providing immediate and accurate glucose monitoring for diabetic patients and the like over an extended time period. In this regard, considerable research and design effort has been directed to in vivo performance of an enzymatic assay. Unfortunately, a glucose oxidase reaction requires a stoichiometric excess of oxygen ($O_2$) in order to yield an accurate indication of glucose concentration, but human blood has a substantial deficiency of oxygen. Although sensors have been developed with differential diffusion components aimed at insuring the presence of excess oxygen at a reaction site, such sensors have utilized electrochemical wire electrodes to measure fluid conductivity changes. This use of wire electrodes inherently requires conductive leads for passing electrical signals into the body of the patient, wherein these electrical signals must be appropriately shielded and/or filtered to minimize or eliminate inaccuracies attributable to electrical interference. As a result, electrode glucose sensors have been difficult in implement in a desirably compact and cost-efficient sensor package which can economically be discarded after use.

There exists, therefore, a need for further improvements in glucose sensors of a type adapted for in vivo implantation, wherein a sensor probe includes alternative means for monitoring an in vivo enzymatic reaction in the presence of excess oxygen. The present invention, which includes optical sensor means, fulfills this need and provides further related advantages.

SUMMARY OF THE INVENTION

In accordance with the invention, an improved glucose sensor is provided for implantation into the body of a patient, and for use in vivo to monitor glucose concentration level. The improved glucose sensor comprises one or more optical fiber optrodes encased within a semipermeable probe housing designed for differential diffusion of glucose and oxygen ($O_2$). Optical monitoring of the optrodes provides an indication of glucose concentration.

In one preferred form, the glucose sensor includes a pair of optical fibers forming part of a transcutaneously extending cable. The fibers terminate at distal ends defining a corresponding pair of optrodes disposed within the semipermeable probe housing. The probe housing includes a generally cylindrical sleeve formed from a material such as silicone permeable to oxygen, but substantially impermeable to glucose. A distal end of the sleeve carries a disk-shaped membrane of a hydrogel material or the like permeable to both glucose and oxygen, wherein the membrane has a substantially smaller surface area in comparison with the cylindrical sleeve. As a result of this differential surface area, glucose entrained in the patient blood stream is allowed to diffuse through the membrane into the sensor interior, together with a substantial excess of entrained oxygen which is permitted to diffuse through the membrane and the sleeve.

The optrodes have distal ends supported within the sensor in spaced relation to each other. A gel material such as albumin conveniently fills the interior of the probe housing to maintain the optrodes in a desired spatial array. One of the optrodes comprises an enzyme optrode having a portion thereof coated with a selected enzyme such as glucose oxidase. An oxygen sensitive coating such as a fluorescent dye is also present on the enzyme optrode, in close proximity with the enzyme coating. The second electrode comprises a reference electrode having the oxygen sensitive coating thereon at a position spaced from the enzyme optrode.

In use, the enzyme coating functions to drive an enzymatic reaction, catalyzing glucose in the presence of excess oxygen to produce gluconic acid and hydrogen peroxide. The oxygen sensitive coating on the enzyme optrode fluoresces with an activity level inversely proportional to oxygen depletion occurring as a result of the enzymatic reaction. The oxygen sensitive coating on the reference electrode fluoresces with a different energy level independent of the enzymatic reaction. Appropriate connection of the optrodes via the cable to an externally located optical monitor permits differential comparison of the fluorescent activities for the two optrodes, wherein this comparison is the result of oxygen depletion attributable to the enzymatic reaction. Such oxygen depletion is correlated directly with glucose concentration level in the blood stream.

In an alternative preferred form of the invention, a single optical fiber optrode may be provided with a first oxygen sensitive coating disposed in close proximity with an enzyme coating, as previously described. A second oxygen sensitive coating adapted to fluoresce with a different characteristic wave length is positioned on the optrode in spaced relation to the enzymatic reaction site. Optical monitoring of the fluorescent activities for the two oxygen sensitive coatings may be correlated with glucose concentration level.

Other features and advantages of the present invention will become more apparent from the following detailed description, taken in conjunction with the accompanying drawings which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENTS

Figure 1:
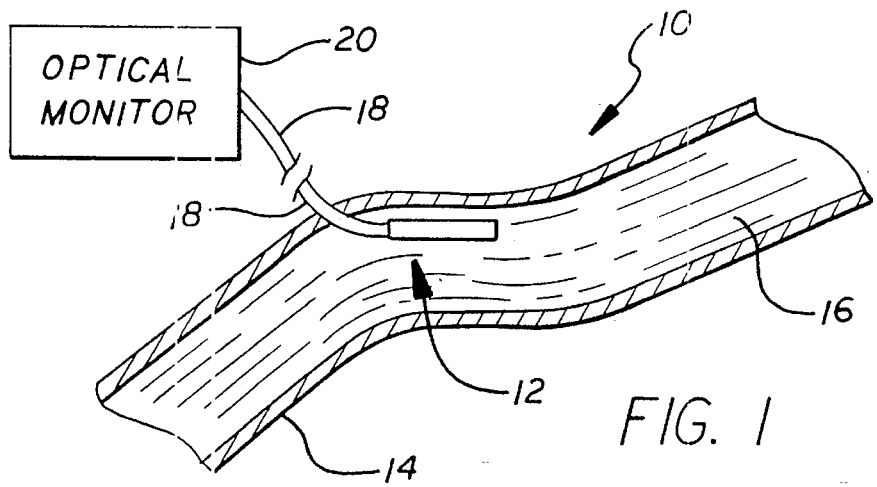
FIG. 1 is a fragmented and somewhat schematic diagram illustrating in vivo implantation and use of an improved optical glucose sensor embodying the novel features of the invention.

As shown in the exemplary drawings, an improved glucose sensor system referred to generally by the reference numeral 10 is provided for in vivo monitoring of glucose concentration level in a patient. The glucose sensor system 10 generally comprises a compact and implantable detector probe 12 adapted for placement directly into a patient blood vessel 14 for direct probe contact with patient blood 16. The detector probe 12 performs an enzymatic assay which can be optically monitored by means of a fiber optic cable 18 connected to an externally positioned optical monitor 20.

The glucose sensor of the present invention beneficially permits the glucose concentration level in patient blood to be monitored continuously or at frequent intervals, with substantially immediate concentration level readings of high reliability and accuracy. The system utilizes one or more optical fibers within the fiber optic cable 18 for monitoring the enzymatic assay, without requiring passage of electrically conductive elements into the body of the patient. As a result, the detector probe 12 may have a highly compact size and shape and functions with minimal patient discomfort or inconvenience to provide regular glucose readings.

Figure 2:
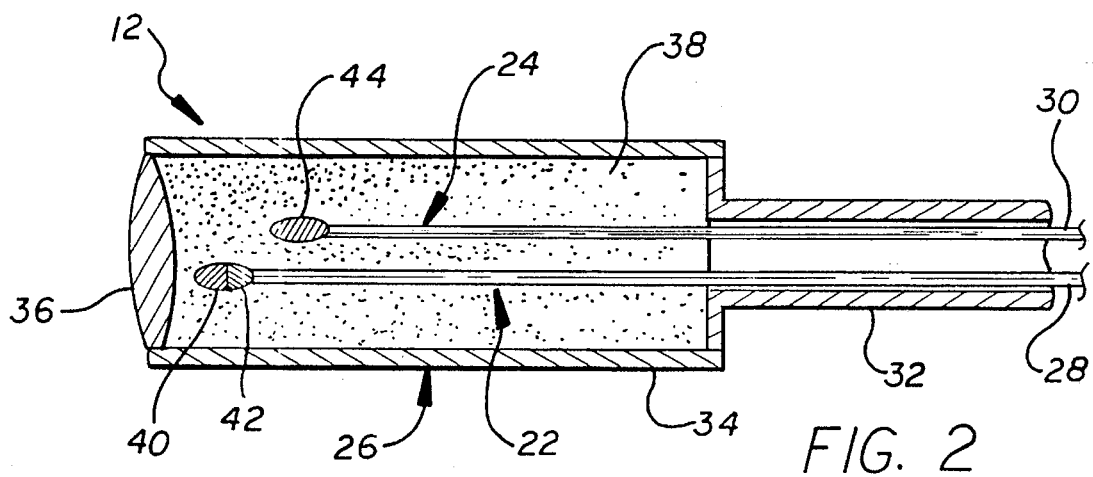
FIG. 2 is an enlarged fragmented sectional view illustrating the glucose sensor of FIG. 1.

As shown in more detail in FIG. 2, the detector probe 12 comprises, in one preferred form, a pair of optical fiber optrodes 22 and 24 mounted within a compact semipermeable probe housing 26. The optrodes 22 and 24 essentially comprise a pair of optical fibers 28 and 30 which extend through a hollow protective cable sheath 32 for transcutaneous implantation by means of a catheter (not shown) or the like. The cable 32 is connected between the probe housing 26 and the externally located monitor 20.

The probe housing 26 is designed for differential diffusion of glucose and oxygen gas ($O_2$) present within the patient's blood stream. In general terms, the housing 26 is designed for limited glucose ingress in combination with a significantly greater proportional ingress of oxygen to the probe interior. With this construction, an enzymatic reaction occurring within the probe, as will be described in more detail, is permitted to proceed in an environment containing a stoichiometric excess of oxygen.

More particularly, the probe housing 26 comprises a generally cylindrical sleeve 34 having a proximal end appropriately attached to the cable sheath 32. The sleeve 34 is constructed from a selected semipermeable material to permit diffusion passage of oxygen substantially in the absence of glucose. A preferred sleeve material comprises a pliable silicone base material such as that marketed by Dow Corning Corporation of Midland, Mich. under the name Silastic.

The opposite or distal end of the sleeve 34 is closed by a disk-shaped membrane 36 of an appropriate material chosen for diffusion passage of glucose. A preferred membrane material comprises a selected hydrogel capable of diffusion ingress of both glucose and oxygen from the blood stream. Notably, the overall surface area of the disk-shaped membrane 36 is substantially less than the total surface area provided by the oxygen permeable sleeve 34, whereby the proportional diffusion ingress of oxygen exceeds the diffusion ingress of glucose. The specific dimensional comparison between the sleeve 34 and membrane 36 is chosen to yield a stoichiometric excess of oxygen within the probe housing 26.

The optrodes 22 and 24 are supported in spaced array in a sensor chamber defined by the interior of the probe housing 26. The optrodes are supported and retained in spaced relation by an appropriate support medium adapted to accommodate diffusion passage of both glucose and oxygen. A preferred support medium 38 comprises a gel material such as albumin.

The optrode 22 comprises an enzyme optrode having an enzyme coating 40 such as glucose oxidase on a distal or tip end thereof. An oxygen sensitive coating 42 is also carried on the enzyme optrode 22 at a position adjacent to the enzyme coating 40. The second optrode 24 comprises a reference optrode having a second oxygen sensitive coating 44 at a distal or tip end thereof. Importantly, the oxygen sensitive coatings 42 and 44 on the two optrodes are spaced from each other.

In use, the enzyme coating 40 on the optrode 22 drives an enzymatic reaction to catalyze glucose in the presence of oxygen ($O_2$), and thereby produce gluconic acid and hydrogen peroxide. With the probe construction as previously described, this enzymatic reaction proceeds in the presence of a stoichiometric excess of oxygen. The oxygen sensitive coating 42 on the enzyme optrode 22 fluoresces with a level of activity or intensity proportional to the oxygen ($O_2$) depletion attributable to the enzymatic reaction. By contrast, the oxygen sensitive coating 44 on the reference optrode 24 fluoresces with a level of activity which is independent of the enzymatic reaction. A variety of different fluorescent dyes which exhibit an oxygen responsive activity are known in the art, such as sodium fluorescein isothiocyanate, perylene dibutyrate and the like, having a characteristic light intensity inversely proportional to oxygen concentration.

Monitoring of the fluorescent activity of the oxygen sensitive coatings 42 and 44, by means of the optical monitor 20, provides a direct measurement of oxygen depletion attributable to the enzymatic reaction. As is known in the art, this depletion of oxygen has a substantially linear relationship to glucose concentration level, whereby the oxygen depletion measurement can be correlated directly with glucose concentration level. The reference optrode 24 conveniently provides a reference standard or base against which the oxygen depletion can be monitored on a continuous basis. In one alternative form, the reference threshold may be known such that the reference optrode 24 can be omitted.

Figure 3:
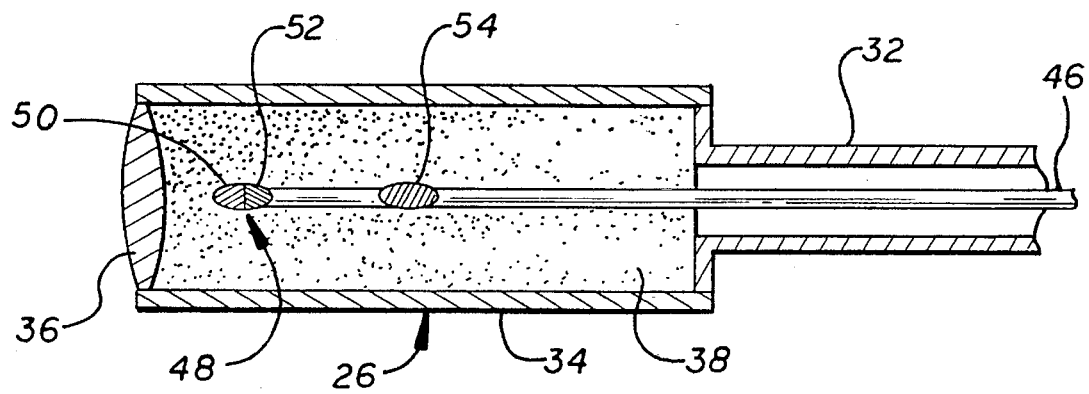
FIG. 3 is an enlarged fragmented sectional view similar to FIG. 2, but depicting one alternative preferred form of the invention.

FIG. 3 illustrates an alternative preferred form of the invention, wherein a single optical fiber 46 extends into the semipermeable probe housing 26 to provide a single optrode 48 used to determine glucose concentration level. As shown, the optrode 48 has an enzyme coating 50 such as glucose oxidase on a tip end in close proximity with an oxygen sensitive coating 52. The enzyme coating 50 initiates the enzymatic reaction, as described with respect to the previous embodiment, and the adjacent oxygen sensitive coating 52 fluoresces with an activity level representative of oxygen depletion attributable to the enzymatic reaction. A second oxygen sensitive coating 54 is placed onto the optrode at a position spaced from the enzymatic reaction, wherein the second coating 54 comprises a different substance adapted to fluoresce with a wavelength which is different from the fluorescing wavelength of the coating 52. The wavelengths from the two coatings 52 and 54 can then be monitored in the same manner as previously described to monitor reaction depletion of oxygen and provide a corresponding indication of glucose concentration level.

The improved glucose sensor of the present invention thus provides a convenient and compact optical system for implementation into an in vivo probe used for in vivo monitoring of a glucose-indicative enzymatic assay.

A variety of further modifications and improvements to the invention described herein will be apparent to those skilled in the art. Accordingly, no limitation on the invention is intended by way of the foregoing description and accompanying drawings, except as set forth in the appended claims.

What is claimed is:

1. A glucose sensor, comprising:

a semipermeable probe housing defining an interior sensor chamber, said housing being formed from a material permeable to glucose and oxygen ($O_2$) entrained in a patient fluid and adapted to be contacted therewith; and optrode means for monitoring glucose concentration in the patient fluid, said optrode means being disposed within said sensor chamber and comprising an enzyme optrode including a first optical fiber having a selected enzyme coating thereon for generating an enzymatic reaction to catalyze glucose in the presence of oxygen ($O_2$), and an oxygen sensitive coating on said first optical fiber at a position to generate a light signal representative of oxygen ($O_2$) depletion in response to the enzymatic reaction, and a reference optrode having an additional oxygen sensitive coating on a second optical fiber at a position spaced from said enzyme and oxygen sensitive coatings on said first optical fiber;

said optrode means further including means for supporting and retaining said first and second optical fibers in a spaced array within said housing, said supporting and retaining means comprising a gel permeable to glucose and oxygen.

2. The glucose sensor of claim 1 wherein said probe housing has a first portion formed from a material permeable to oxygen ($O_2$) and substantially impermeable to glucose, and a second portion formed from a material permeable to glucose, said first portion having a surface area for exposure to the patient fluid which is substantially greater than a surface area of said second portion for exposure to the patient fluid, whereby the enzymatic reaction occurs with a stoichiometric excess of oxygen ($O_2$).

3. The glucose sensor of claim 2 wherein said first portion is formed from a silicone material.

4. The glucose sensor of claim 2 wherein said second portion is formed from a material permeable to glucose and oxygen ($O_2$).

5. The glucose sensor of claim 4 wherein said second portion is formed from a hydrogel.

6. The glucose sensor of claim 1 wherein said enzyme coating is glucose oxidase.

7. The glucose sensor of claim 1 wherein said oxygen sensitive coating is a fluorescent dye.

8. The glucose sensor of claim 1 further including an optical monitor connected to said at least one optical fiber.

9. A glucose sensor, comprising:

a semipermeable probe housing defining an interior sensor chamber, said housing being formed from a material permeable to glucose and oxygen ($O_2$) entrained in a patient fluid and adapted to be contacted therewith; and optrode means for monitoring glucose concentration in the patient fluid, said optrode means being disposed within said sensor chamber and including an optical fiber having a selected enzyme coating thereon for generating an enzymatic reaction to catalyze glucose in the presence of oxygen ($O_2$), said optrode means further including a first oxygen sensitive coating on said optical fiber at a position in close proximity to said enzyme coating to generate a light signal representative of oxygen ($O_2$) depletion in response to the enzymatic reaction;

and a second oxygen sensitive coating on said optical fiber at a position spaced from said enzyme and first oxygen sensitive coatings, said first and second oxygen sensitive coatings responding to the presence of oxygen to generating light signals of different wave lengths.

10. A glucose sensor adapted for in vivo implantation into the body of a patient, said sensor comprising:

a semipermeable probe housing defining an interior sensor chamber, said housing being formed from a material permeable to glucose and oxygen ($O_2$) entrained in a patient fluid and adapted to be contacted therewith; and optrode means for monitoring glucose concentration in the patient fluid, said optrode means including an enzyme optrode having a first optical fiber adapted for transcutaneous passage into the body of a patient and having a distal end disposed within said sensor chamber, an enzyme coating on said first fiber generally at said distal end for generating an enzymatic reaction to catalyze glucose in the presence of oxygen ($O_2$), and an oxygen sensitive coating on said first fiber generally at said distal end in close proximity with the enzyme coating to generate a light signal representative of oxygen ($O_2$) depletion in response to the enzymatic reaction, and a reference optrode having an additional oxygen sensitive coating on a second optical fiber at a position spaced from said enzyme and oxygen sensitive coatings on said first optical fiber;

said optrode means further including means for supporting and retaining said first and second optical fibers in a spaced array within said housing, said supporting and retaining means comprising a gel permeable to glucose and oxygen.

11. The glucose sensor of claim 10 wherein said housing has a first portion formed from a material permeable to oxygen ($O_2$) and substantially impermeable to glucose, and a second portion formed from a material permeable to glucose, said first portion having a surface area for exposure to the patient fluid which is substantially greater than a surface area of said second portion for exposure to the patient fluid, whereby the enzymatic reaction occurs with a stoichiometric excess of oxygen ($O_2$).

12. The glucose sensor of claim 10 further including an optical monitor for connection to a proximal end of said fiber outside the body of the patient.

* * * * *